United States Patent
Tashjian et al.

(12)
(10) Patent No.: US 6,518,229 B2
(45) Date of Patent: Feb. 11, 2003

(54) ANTIBACTERIAL COMPOSITION COMPRISING AN AMPHOTERIC/ANIONIC SURFACTANT MIXTURE

(75) Inventors: Anne Tashjian, River Edge, NJ (US); Susan Mills, Ringwood, NJ (US); Marie Lewis, Chestnut Ridge, NY (US)

(73) Assignee: Playtex Products, Inc., Westport, CT (US)

( * ) Notice: Subject to any disclaimer, the term of this patent is extended or adjusted under 35 U.S.C. 154(b) by 15 days.

(21) Appl. No.: 09/730,907

(22) Filed: Dec. 6, 2000

(65) Prior Publication Data

US 2002/0103092 A1 Aug. 1, 2002

(51) Int. Cl.$^7$ ............................. C11D 1/94; C11D 3/48
(52) U.S. Cl. .................. 510/131; 510/130; 510/138; 510/119; 510/123; 510/124; 510/382; 510/388; 510/433; 510/426; 510/427
(58) Field of Search ................. 510/130, 131, 510/138, 119, 123, 124, 382, 388, 433, 426, 427

(56) References Cited

U.S. PATENT DOCUMENTS

| | | | |
|---|---|---|---|
| 4,186,113 A | 1/1980 | Verdicchio et al. | 252/526 |
| RE30,641 E | 6/1981 | Verdicchio et al. | 252/526 |
| 4,636,329 A | 1/1987 | Steuri | 252/106 |
| 4,681,704 A | 7/1987 | Bernardino et al. | 252/546 |
| 5,000,868 A | 3/1991 | Wittpenn, Jr. et al. | 252/106 |
| 5,139,705 A | 8/1992 | Wittpenn, Jr. et al. | 252/547 |
| 5,290,482 A | 3/1994 | Marschner et al. | 252/544 |
| 5,346,639 A | 9/1994 | Hatfield | 252/90 |
| 5,435,933 A | 7/1995 | Subramanyam et al. | 252/108 |
| 5,487,843 A | 1/1996 | Coyle et al. | 252/89.1 |
| 5,512,199 A | 4/1996 | Khan et al. | 252/106 |
| 5,571,501 A | 11/1996 | Toy | 424/49 |
| 5,629,276 A | 5/1997 | Subramanyam et al. | 510/133 |
| 5,646,100 A | * 7/1997 | Haugk et al. | 510/131 |
| 5,653,970 A | * 8/1997 | Vermear | 424/70.24 |
| 5,681,802 A | * 10/1997 | Fujiwara et al. | 510/130 |
| 5,747,436 A | 5/1998 | Patel et al. | 510/124 |
| 5,767,051 A | 6/1998 | Drapier et al. | 510/235 |
| 5,792,737 A | 8/1998 | Grüning et al. | 510/126 |
| 5,977,049 A | * 11/1999 | Briceno et al. | 510/387 |
| 6,008,173 A | * 12/1999 | Chopra et al. | 510/152 |
| 6,165,454 A | * 12/2000 | Patel et al. | 424/70.11 |

* cited by examiner

*Primary Examiner*—Charles Boyer
(74) *Attorney, Agent, or Firm*—Ohlandt, Greeley, Ruggiero & Perle, LLP

(57) ABSTRACT

An antibacterial composition is provided that has an anionic surfactant, an amphoteric surfactant, a cationic conditioning agent, an antibacterial agent and water. Preferably, the composition is a liquid hand soap. The aqueous antibacterial composition, especially when an antibacterial liquid hand soap, has a proper balance of ingredients for providing a high cleansing ability, high foam, good conditioning and a pleasant emollient effect on the skin. The method of reducing amount of bacteria on part of a person's body, such as a hand, includes contacting the hand with the composition and, thereafter, rinsing the hand with water.

16 Claims, No Drawings

ANTIBACTERIAL COMPOSITION COMPRISING AN AMPHOTERIC/ANIONIC SURFACTANT MIXTURE

BACKGROUND OF THE INVENTION

1. Field of the Invention

The present invention relates to an antibacterial composition that can be used in a body wash, hand soap or shampoo. In particular, the present invention relates to an antibacterial liquid hand soap. It also relates to a method of reducing the amount of bacteria on a part of a person's body, such as a person's hand.

2. Description of the Prior Art

Good detergent properties, especially in a soap, can be obtained by using one of the following: an anionic detergent or surfactant, a non-ionic surfactant, and to some extent, an amphoteric surfactant. However, to obtain a high level of foam, an amphoteric surfactant, such as a sultaine, is used to function as a foam booster.

To obtain a composition, such as a soap, that has a pleasant feel on the skin, a conditioning agent with emollient properties is generally used. However, such a conditioning agent is a cationic compound that generally is not compatible with the anionic detergent. Hence, the cationic compound causes a reduction in the detergent properties of the composition, especially a soap composition. In addition, such a cationic compound can also complex with the sultaine resulting in a reduction in the amount of foam.

U.S. Pat. No. 5,747,436 to Patel et al. provides a conditioning shampoo having enhanced antistatic properties that has a surfactant mixture of an anionic detergent, an amphoteric surfactant and a conditioning agent; a static control mixture of di-quaternary ammonium salts; and water. This composition is shampoo, not an antibacterial hand soap.

U.S. Pat. No. 5,571,501 to Toy is directed to an aqueous based oral composition that has potassium salt of Triclosan as the antibacterial agent. U.S. Pat. No. 5,629,276 to Subramanyam et al. and U.S. Pat. No. 5,646,100 to Haugk et al. describe compositions having Triclosan.

U.S. Pat. No. 5,512,199 to Khan et al. is directed to hand wipe formulations that require no scrubbing, washing and rinsing.

U.S. Pat. No. 5,435,933 to Subramanyam et al. is directed to a personal cleansing composition in bar form.

U.S. Pat. No. 4,681,704 to Bernardino et al. is directed to a detergent composition for removing greasy soils having water-soluble amine oxides.

U.S. Pat. No. 5,767,051 to Drapier et al. is directed to clear light duty liquid cleaning composition.

U.S. Pat. No. 5,792,737 to Grüning et al. is directed to an aqueous surfactant preparation having betaines of a specific formula.

Other detergents are disclosed in U.S. Pat. No. 4,186,113 and the related Reissue Pat. No. 30,641 to Verdicchio et al.; U.S. Pat. No. 4,636,329 to Steuri; U.S. Pat. Nos. 5,000,868 and 5,139,705, both to Wittpenn, Jr. et al.; U.S. Pat. No. 5,290,482 to Marschner et al.; U.S. Pat. No. 5,346,639 to Hatfield; and U.S. Pat. No. 5,487,843 to Coyle et al.

While the above compositions have some of the ingredients of the present invention, none have an anionic surfactant, an amphoteric surfactant, a cationic conditioning agent, an antibacterial agent and water in a liquid soap or composition, let alone the combination of surfactants of the present invention. Furthermore, the prior art compositions do not recognize the need for balance of the above ingredients to provide an antibacterial soap. Thus, such compositions do not provide a balance of effective cleansing, high foam and emollient benefits, without irritating the skin, all of which are achieved by the soap of the present invention.

SUMMARY OF THE INVENTION

It is an object of the present invention to provide an antibacterial composition.

It is another object of the present invention to provide an antibacterial liquid hand soap or composition.

It is yet another object of the present invention to provide such a soap that has a balance of effective cleansing, high foam and emollient benefits without irritating the skin.

It is still another object of the present invention to provide such a composition that is aqueous.

It is a further object of the present invention to provide such a composition that has a unique combination of surfactants.

It is still a further object of the present invention to provide a method of reducing the amount of bacteria on a hand.

These and other objects of the present invention will become apparent from an antibacterial composition that has an anionic surfactant, an amphoteric surfactant, a cationic conditioning agent, an antibacterial agent, and water. The combination of surfactants preferably includes a sultaine and a betaine. Preferably, the antibacterial composition is a liquid hand soap.

The present invention also includes a method of reducing the amount of bacteria on a person's body, such as a person's hand. The method includes contacting the hand with a composition according to the present invention that has an amount of an antibacterial agent effective for reducing the amount of bacteria on the hand; and thereafter rinsing the hand with water.

DETAILED DESCRIPTION OF THE INVENTION

It has now been discovered that it is possible to formulate an antibacterial composition, especially a liquid hand soap, that has a proper balance of ingredients for providing a high cleansing ability, high foam, good conditioning and a pleasant emollient effect on the skin.

The present antibacterial composition includes an anionic surfactant, an amphoteric surfactant, a cationic conditioning agent, an antibacterial agent, and water. Preferably, the present antibacterial composition is a liquid hand soap.

Such compositions according to the present invention can be prepared in clear or opaque form. They are highly detersive but non-irritating to the skin. Also, they are hypoallergenic, and have high foam and good emollient properties.

The anionic surfactant provides detergent properties to the antibacterial liquid hand soap for cleansing the skin. The anionic surfactant can be any anionic surfactant that has detergent properties including an anionic detergent. The preferred anionic surfactant or detergent includes sodium laureth sulfate, sodium lauryl sulfate, disodium oleamido MEA sulfosuccinate, and mixtures thereof. Preferably, the anionic surfactant is about 5 percentage by weight or weight percent (wt %) to about 9 wt % of the total weight of the composition. More preferably, the anionic surfactant is about 5.85 wt % to about 8.75 wt %.

The amphoteric surfactant provides thickening and high foam property to the soap. It is a foam booster. Thus, it improves foaming of the soap. The preferred classes of amphoteric surfactant are sultaines and betaines. Preferably, the amphoteric surfactant is a sultaine. Most preferably, the amphoteric surfactant is a mixture of a sultaine and a betaine.

The preferred sultaine is cocamidopropyl hydroxysultaine. The preferred betaine is cocamidopropyl betaine. Preferably, the total amount of amphoteric surfactant is about 1 wt % to about 3 wt % of the total weight of the composition. More preferably, the total amount of amphoteric surfactant is about 1.4 wt % to about 2.2 wt % of the total weight of the composition. In the preferred embodiment, the amphoteric surfactant is about 0.8 wt % to about 1.2 wt % sultaine, and about 0.6 wt % to about 1 wt % betaine.

A significant feature of one of the most preferred embodiments of the present invention is the surfactant blend that includes sodium laureth sulfate, sodium lauryl sulfate, disodium oleaimido MEA sulfosuccinate, all of which are anionic surfactant, cocamidopropyl betaine, which is an amphoteric surfactant and cocamide MEA, which is a non-ionic surfactant. Besides the surfactant blend, there should also be the amphoteric surfactant cocamidopropyl hydroxysultaine. It this most preferred embodiment, the surfactant blend is about 20 wt %, while the cocamidopropyl hydroxysultaine is about 2.0 wt % of the total weight of the composition.

The cationic conditioning agent is included for producing an emollient effect on the skin. The cationic conditioning agent can be Polyquaternium-4, Polyquaternium-7, Polyquaternium-10, or any combination thereof. Preferably, the cationic conditioning agent is Polyquaternium-7. Preferably, the cationic conditioning agent is about 0.1 wt % to about 0.3 wt % of the total weight of the composition. More preferably, the total amount of cationic conditioning agent is about 0.22 wt % of the total weight of the composition.

To obtain a liquid composition, especially a hand soap, that has antibacterial activity, an antibacterial agent or bacteriostat is added to composition. The preferred antibacterial agent is Triclosan. Preferably, the Triclosan is about 0.16 wt % to about 0.24 wt % of the total weight of the composition and, more preferably, it is about 0.2 wt % of the total weight of the composition.

The antibacterial liquid hand soap composition should also be in a medium. Preferably, the medium is water due to its low cost. The medium produces the proper viscosity for the soap. When the medium is water, it is preferably present in an amount about 82 wt % to about 88 wt % of the total weight of the composition.

The antibacterial composition, especially a liquid hand soap composition, may further have a non-ionic surfactant. The non-ionic surfactant is included to augment the detersive properties of the composition and boost its cleansing action. The non-ionic surfactant can be any non-ionic compound that has surfactant properties. The preferred non-ionic surfactants include cocamide MEA, oleaimide MEA, and mixtures thereof. Preferably, the non-ionic surfactant is about 0.25 wt % to about 0.5 wt % of the total weight of the composition. More preferably, the total amount of the non-ionic surfactant is about 0.28 wt % to about 0.42 wt % of the total weight of the composition.

The antibacterial composition of the present invention, especially when the composition is a liquid hand soap, can further include one or more additives that are commonly used in soaps. Such additives include a thickening agent, a preservative, a fragrance, a colorant and a pH adjuster.

A preferred thickening agent is sodium chloride. It is preferably present in an amount less than 1 wt %, preferably less than about 0.75 wt %, of the total weight of the composition.

A preferred preservative is DMDM hydantoin. It is preferably present in an amount about 0.3 wt % to about 0.5 wt %, and more preferably about 0.3 wt % to about 0.4 wt %, of the total weight of the composition.

A preferred pH adjuster is citric acid. It is present in an amount about 0.02 wt % of the total weight of the composition.

In a more preferred embodiment of the present invention, the antibacterial composition, especially when a liquid hand soap, has sodium laureth sulfate, sodium lauryl sulfate, disodium oleaimido MEA sulfosuccinate, cocamidopropyl hydroxysultaine, cocamidopropyl betaine, Polyquaternium-7, Triclosan, cocamide MEA and water.

The pH of the antibacterial liquid hand soap composition is from about 5 to about 7. At such a pH range, the composition in any form, but especially as an antibacterial liquid hand soap composition, is both stable and capable of providing a balance of effective cleansing, high foam and emollient benefits without irritating the skin. This high foam means that it has high foam initially (called blast foam) and lasts for a period of time thereafter. More preferably, the pH of the antibacterial liquid hand soap composition is from about 5.5 to about 6.5.

The present invention also includes a method of reducing amount of bacteria, especially on a hand. The method includes contacting the desired area, or a hand, with an effective amount of a composition according to the present invention, and thereafter, rinsing the hand with water.

The Examples that follow are intended for illustrating the present invention and not for limiting the scope thereof.

EXAMPLES

Two antibacterial liquid hand soap compositions, FORMULA A, FORMULA B and FORMULA C, are depicted below:

| FORMULA A | |
|---|---|
| INGREDIENT | Active Wt % |
| Water, Deionized | 87.2 |
| Surfactant Blend | 8.4 |
| Sodium Laureth Sulfate | |
| Sodium Lauryl Sulfate | |
| Disodium Oleamido MEA Sulfosuccinate | |
| Cocamidopropyl Betaine | |
| Cocamide MEA | |
| Polyquaternium-7 | 2.5 |
| Cocamidopropyl Hydroxysultaine | 1.0 |
| Others (for example, preservative, fragrance, pH adjuster & colorant | 0.7 |
| Triclosan (Bacteriostat) | 0.2 |

| FORMULA B | |
|---|---|
| INGREDIENT | Wt % |
| Water, Deionized | 86.5 |
| Surfactant Blend | 8.4 |
| Sodium Laureth Sulfate | |
| Sodium Lauryl Sulfate | |
| Disodium Oleamido MEA Sulfosuccinate | |
| Cocamidopropyl Betaine | |
| Cocamide MEA | |
| Polyquaternium-7 | 2.5 |
| Cocamidopropyl Hydroxysultaine | 1.0 |
| Others (for example, thickening agent, preservative, fragrance, pH adjuster & colorant | 1.4 |
| Triclosan | 0.2 |

| FORMULA C | |
|---|---|
| INGREDIENT | Wt % |
| Water, Deionized | 85.8 |
| Surfactant Blend | 8.4 |
| Sodium Laureth Sulfate | |
| Sodium Lauryl Sulfate | |
| Disodium Oleamido MEA Sulfosuccinate | |
| Cocamidopropyl Betaine | |
| Cocamide MEA | |
| Polyquaternium-7 | 2.5 |
| Cocamidopropyl Hydroxysultaine | 1.0 |
| Sodium Chloride | 0.4 |
| DMDM Hydantoin | 0.3 |
| Others (for example, thickening agent, preservative, fragrance, pH adjuster & colorant | 1.4 |
| Triclosan | 0.2 |

It is believed that the antibacterial composition of the present invention can be used in other forms, not just as a liquid hand soap. For example, it is believed that the composition can be made into a body wash. It is also believed that the composition can be a shampoo for the hair.

The use of singular in the present application can also mean plural for the same ingredient. The present invention having been described with particular reference to the preferred forms thereof, it will be obvious that various changes and modifications may be made herein without departing from the spirit and the scope of the invention as defined in the appended claims.

We claim:

1. An antibacterial composition, comprising:
    an anionic surfactant;
    an amphoteric surfactant having:
        (i) a sultaine selected from the group consisting of cocamidopropyl hydroxysultaine; and
        (ii) a betaine;
    a cationic conditioning agent;
    an antibacterial agent; and
    a medium,
    wherein said sultaine is about 0.8 wt % to about 1.2 wt % of the total weight of the composition, and
    wherein said betaine is about 0.6 wt % to about 1 wt % of the total weight of the composition.

2. The composition of claim 1, wherein said anionic surfactant is selected from the group consisting of sodium laureth sulfate, sodium lauryl sulfate, disodium oleamido MEA sulfosuccinate, and mixtures thereof.

3. The composition of claim 1, wherein said anionic surfactant is about 5 wt % to about 9 wt % of the total weight of the composition.

4. The composition of claim 1, wherein said cationic conditioning agent is Polyquaternium-7.

5. The composition of claim 1, wherein said cationic conditioning agent is about 0.1 wt % to about 0.3 wt % of the total weight of the composition.

6. The composition of claim 1, wherein said medium is water in an amount about 82 wt % to about 88 wt % of the total weight of the composition.

7. The composition of claim 1, further comprising a non-ionic surfactant selected from the group consisting of cocamide MEA, oleimide MEA, and mixtures thereof.

8. The composition of claim 7, wherein said non-ionic surfactant is about 0.25 wt % to about 0.5 wt % of the total weight of the composition.

9. The composition of claim 1, wherein said antibacterial agent is Triclosan.

10. The composition of claim 1, wherein said antibacterial agent is about 0.1 wt % to about 0.5 wt % of the total weight of the composition.

11. The composition of claim 1, further comprising at least one additive selected from the group consisting of a thickening agent, a preservative, a fragrance, a colorant, a pH adjuster, and mixtures thereof.

12. The composition of claim 1, wherein the pH of the composition is from about 5 to about 7.

13. The composition of claim 1, wherein the composition is an antibacterial liquid hand soap.

14. An antibacterial liquid hand soap composition, comprising:
    an anionic surfactant selected from the group consisting of sodium laureth sulfate, sodium lauryl sulfate, disodium oleimido MEA sulfosuccinate, and any combinations thereof;
    an amphoteric surfactant having cocamidopropyl hydroxysultaine and a betaine; a cationic conditioning agent; a non-ionic surfactant; an antibacterial agent; and water,
    wherein said hydroxysultaine is about 0.8 wt % to about 1.2 wt % of the total weight of the composition, and
    wherein said betaine is about 0.6 wt % to about 1 wt % of the total weight of the composition.

15. An antibacterial liquid hand soap composition, comprising:
    a surfactant blend that includes sodium laureth sulfate, sodium lauryl sulfate, disodium oleaimido MEA sulfosuccinate, cocamidopropyl betaine, and cocamide MEA
    cocamidopropyl hydroxysultaine;
    a cationic conditioning agent;
    an antibacterial agent; and
    water,
    wherein the surfactant blend is about 20 wt %, while the cocamidopropyl hydroxysultaine is about 2.0 wt % of the total weight of the composition.

16. A method of reducing amount of bacteria on a hand, comprising:
    (a) contacting said hand with a composition according to claim 1, said composition comprising an amount of an antibacterial agent effective for reducing the amount of bacteria on said hand; and thereafter
    (b) rinsing said hand with water.

* * * * *